United States Patent [19]
Gallais

[11] Patent Number: 5,350,300
[45] Date of Patent: Sep. 27, 1994

[54] DENTAL IMPLANT

[76] Inventor: Jacques Gallais, 1, Rue de l'Ecrivain, 89. Sens, France

[21] Appl. No.: 675,915
[22] PCT Filed: Oct. 31, 1990
[86] PCT No.: PCT/FR90/00789
§ 371 Date: May 1, 1991
§ 102(e) Date: May 1, 1991
[87] PCT Pub. No.: WO91/07140
PCT Pub. Date: May 30, 1991

[30] Foreign Application Priority Data
Nov. 8, 1989 [FR] France .............. 89 14682

[51] Int. Cl.$^5$ .............................. A61C 8/00
[52] U.S. Cl. ........................ 433/173; 433/141
[58] Field of Search ..................... 433/173, 174

[56] References Cited
U.S. PATENT DOCUMENTS

| | | | |
|---|---|---|---|
| 3,474,537 | 10/1969 | Christensen | 433/174 |
| 4,016,651 | 4/1977 | Kawahara et al. | 433/174 |
| 4,682,951 | 7/1987 | Linkow | 433/173 |
| 4,872,840 | 10/1989 | Bori | 433/173 |
| 4,917,604 | 4/1990 | Small | 433/174 |

FOREIGN PATENT DOCUMENTS

| | | |
|---|---|---|
| 3736977 | 7/1988 | Fed. Rep. of Germany . |
| 2596273 | 10/1987 | France . |
| 9001303 | 2/1990 | PCT Int'l Appl. .......... 433/174 |

*Primary Examiner*—John J. Wilson

[57] ABSTRACT

The invention concerns in combination a dental implant with complete tooling system and the method of installation of the implant in the maxillary of a human being. The implant is divided into two parts namely "the body" and the head. The profile of the body is composed by the combination of conical portions (3) and (5) together with the cylindrical portions (2), (4), (6) and (7). The body is provided with a threaded end (8), which is splitted in the form of two legs (10) and (12); wherein the threaded end (8) is designed to receive the head (9) which can be screwed on the body of the implant. To prevent unscrewing of the head (9), the two legs (10) and (12) are bent into the slots (14) and (16) provided in the head (9). The other end of the body of the implant is provided either with a threaded pin (1) or a threaded hole to receive a dental prosthetic appliance afterwards.

5 Claims, 7 Drawing Sheets

DENTAL IMPLANT

FIELD OF APPLICATION AND THE BACKGROUND OF THE INVENTION

The present invention concerns a new dental implant system, comprising a dental implant, a complete tooling system accompanied with a medical and surgical operation procedure necessary for the installation of the said implant into the maxillary of humain beings. The implantology itself is not a novel science. A large number of experiments had been carried out for the restoration of the mastication capacity and to reconstitute the aesthetic defects and consequently the specialists practicing this particular art were always in search of a suitable solution which may be classified either as "Endo-osseous" or as "Sub-osseous" type, capable to replace the defective tooth, which were made of different materials such as stone by AZTEQUE, ivory by FAUCHARD, platinium or bronze by YOUNGER, GREENFIELD, LEGER, DOREZ, or others. Those research workers were known as the pioneer or the first implantologists just after the second world war, and among them, FORMIGGINI was known as the principal creator of the modern "Endo-osseous type" implant system. His implant comprised a metal wire wound axially on a metal rod. The said system was modified and improved by CHERCHEVE in the form of a helicoidal screw which is the origine of all dental implants utilized actually. In 1959 BENHAIM and ACHARD presented for the first time a tubular implant. On the other hand, the other research workers were working on different systems. We can mention SCIALLOM, whose NEEDLE TYPE IMPLANTS found a number of disciples, LINCOW the inventor of BLADE TYPE IMPLANTS, JUILLET whoe realised the T3D system and SCORTECCI and SANDHAUS took back the transvestibular system, where the C.B.S. became well known as the origine of "Frialits" and other ceramic screws. Though all the above mentioned "Endo-osseous type" dental implants were developped in the past, a very high number of unsuccessful attempts were reported and consequently this particular discipline remained in the darkness from 1970 to 1982.

In 1983 BRANEMARK in collaboration with ZARB and ALBREKSTON reintroduced the dental implantology with a screw type implant. The Americans followed closely. NIZNIC inspired by the works of BENHAIM and CHERCHEVE reintroduced again a tubular implant and a spiral type implant known respectively as "CORE-VENT" and "SCREW-VENT". Although the different modifications do not go beyond some details concerning the structure of those implants, the principal modification in the field of implantology is obtained through the utilization of new materials having very high osteogenic potential such as titan, calcium ceramics, bio-glass, synthetic polymers and lastly through utilization of surface treatments. The enormous progress realized in the field of modern metallurgy by the space research organizations can be considered as the fundamental foundation of implantology, such as bio-compatibility, bio-thermal and bio-functional capacity. Thus the modern implantology became a multidisciplinary technology, resulting from a close collaboration between medical and engineering research workers, specialized in the different subjects. Their works are crowned by the deposit of more than hundred patents in less than three years.

Actually the "Screw type" implants retained into the bone with the help of screw threads are mostly utilized. But attention is drawn on the fact that the spongy bones, brittle and covered by a thin layer of cortical do produce an ideal support for screwing which is necessary to support the alternative shearing forces produced on the thread surfaces during chewing operation. Consequently in this particular invention I am searching for a novel type of implant utilizing a new and precise implantation technology which as far as my knowledge were never utilized before. The principal goal of this invention is to propose a solution which will permit to avoid screw threads into the spongy bones and consequently to increase considerably the bearing surface of the implant in contact with the bone and thus producing a substantial reduction of the intensity of pressure exerted on the said bearing surface during the chewing operation.

BRIEF DESCRIPTION OF THE INVENTION

Uptil now, in the field of dental implant technology, any penetration inside the upper maxillary cavity is carefully avoided. However in some favourable cases the floor of the maxillary sinus and also the floor of the nasal cavity may be utilized profitably as solid platforms for the implantation of dental implants.

Encouraged by the results obtained from the well known operation technic of CALDWELL-LUC concerning maxillary sinus, I see the possibility of the application of a similar technology of intervention to fix a specially profiled dental implant, which is principally divided into two different portions named respectively "the head" and "the body". To install the said body of the implant on the position desired, it is necessary to drill a hole in the maxillary, in such a manner that the profile of the said hole, is perfectly complimentary to the profile of the said implant. Evidently the said hole is realized with the help of a milling tool having the same profile as the body of the implant. The said body of the implant is provided with a threaded and splitted end which can be introduced into the sinus cavity inorder to receive the said head of the implant. The said head can be introduced inside the sinus cavity through another hole prepared before, on the level of the eye tooth cavity. Once the head is introduced in the sinus and placed in the preselected position, a perfect alignement can be obtained for a permanent assembly, by introducing the said body of the implant from the bottom.

In order to achieve this operation, the "head" is retained in position by a special tool designed for this purpose, by utilizing the said cavity in front of the sinus, then the "body" of the implant is screwed into the "head" of the implant in such a manner that the male profile of the body of the implant coincides perfectly with the female complimentary profile drilled previously in the maxillary bone. In this particular stage of operation the splitted portion of the said threaded end of the implant should project beyond the upper surface of the head of the implant. The said upper surface is provided with four slots in which one can bend each leg of the said splitted portion of the implant in opposite direction and thus realizing a perfect anchorage in order to prevent the possibility of separation of the head from the body of the implant in course of utilization. The opposite end of the said implant may contain either a threaded neeple or a threaded hole in order to receive any adequate dental prosthetic appliance afterwards.

The same implant, with very little modification can also be installed inside the nasal cavity. A complete set of implants of different dimension together with all tools necessary for the installation can be manufactured and delivered as completely assembled, sterilized and antiseptic package. However it is also possible to imagine a "throw out" type of tooling system which should be utilized only once.

BRIEF DESCRIPTION OF DRAWINGS

The FIG. 1 shows the profile of a skull and the mandible. The reference A on this figure represents the "eye cavity"; the reference B represents the "under eye hole"; the reference C represents the "nasal cavity"; the reference D represents the opening hole of the sinus; the reference E represents the maxillary bone; the reference F represents the mandible.

The FIG. 2 shows the details of the implant with the "body" and the "head" in assembled position.

The FIGS. 3, 4, 5 and 6 shows the details of the head of the implant.

The FIGS. 7 and 8 show a second mode of realization of the same implant.

The FIG. 9 shows the sectional view of the upper maxillary as represented in the FIG. 10.

The FIG. 10 shows a sectional view where G represents the opening of the maxillary sinus and the implant S in its definitive position.

The FIG. 10A shows a cap.

The FIG. 11 shows the guiding element in position and the maxillary, after the first cylindrical drilling.

The FIG. 12 shows the milling operation of the profiled cavity with a formed tool in place.

The FIG. 13 shows the realization of the spherical portion on the maxillary sinus floor with a second profiled milling tool mounted on a specially adapted drilling element.

The FIG. 14 shows the head of the implant in place.

The FIG. 15 shows the guiding element for drilling.

The FIG. 16 shows the same guiding element after drilling the guiding hole.

The FIG. 17 shows the first profiled milling tool which should be utilized to realize the profiled hole in the maxillary bone intended to receive the implant.

The FIG. 18 shows the detail of the driving element to receive the second profilled milling tool.

The FIG. 19 shows the second profiled milling tool which can be mounted on the driving element as shown in the FIG. 18.

The FIG. 19A shows the definitive assembly of the body with the head of the implant together with the anchoring legs before they are bent in place.

The FIGS. 20 and 21 show a special instrument to maintain the head of the implant in its selected position in course of successive operation procedure for the installation of the said implant.

The FIG. 22 shows a second instrument which can be mounted on the handle of the special instrument shown in the FIGS. 20 and 21.

DETAILED DESCRIPTION OF THE INVENTION

The present invention concerns at first an "Endoosseous type" dental implant as a novel product; secondly a combination of particularly adapted tooling means for the installation of the said implant; and thirdly a particular method to install the said implant preferably but not exclusively in the maxillary of a human being. Dental implants of different dimension together with an assembly of instruments or tools can be packed in a specially designed box to form a single kit.

In order to simplify the description of the invention, the first part of the description is reserved particularly to expose the details of the said dental implant, the second part of the description is reserved to expose the different instruments or tooling systems necessary for the installation of the said implant and the third part of the description is reserved to expose all the sequential operations necessary for the installation of the said implant in the mouth.

Figures 2, 3, 4, 5, 6:
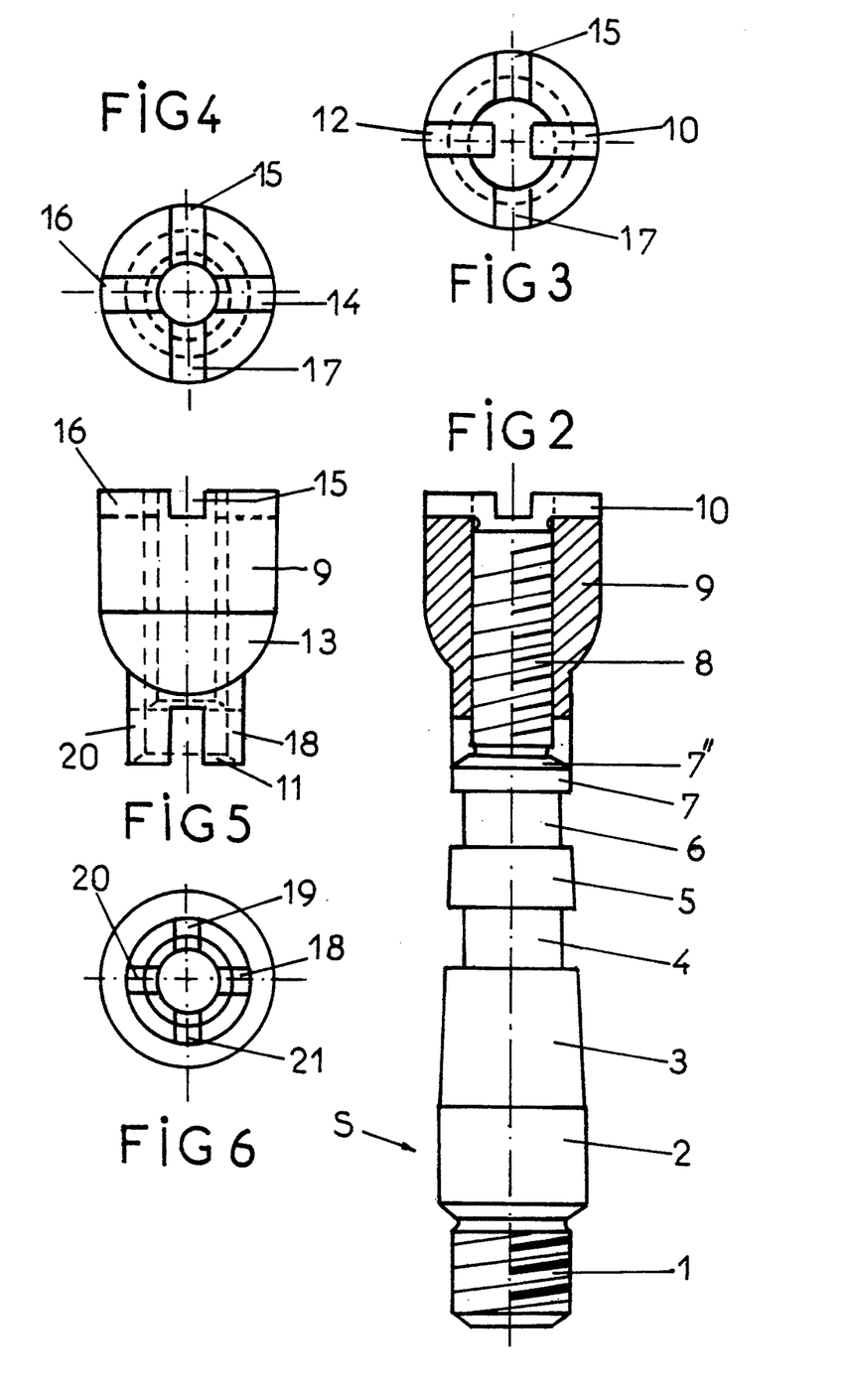

The FIGS. 2 and 3 show a first mode of realization of the said implant according to the present invention represented by the reference S. This implant is divided into two portions called "The body" and "The head". The body of the implant itself is subdivided in a number of portions as follows: One threaded end 1 is provided to receive a dental prosthetic appliance afterwards. The said end is followed by a first cylindrical portion 2, joining with a first truncated conical portion 3. The said portion 3 joins with a second cylindrical portion 4 having a smaller diameter than the smallest diameter of the cone 3. The portion 4 is joined with a second truncated conical portion 5, having the same conicity as the truncated conical portion 3. The two truncated conical portions 3 and 5 are disposed co-axially and their external surfaces are designed in such a manner that they can perfectly coincide with the internal surface of a cavity having the same conicity. The second truncated conical portion 5 is followed by a third cylindrical portion 6 having a diameter smaller than the smallest diameter of the second truncated conical portion 5. The said cylindrical portion 6 is followed by another cylindrical portion 7 having a diameter equal to the diameter obtained by the prolongation of the surfaces of the said truncated conical portions 3 and 5 up to the base of the cylindrical portion 7. The said cylindrical portion 7 is followed by a small surface 7", inclined to 30°, which is joined with the other cylindrical end 8 of the said implant. The said end 8 is provided with a threaded portion where the head 9 of the implant can be screwed in and it is followed by a splitted portion forming two legs 10 and 12 which can be bent inside the grooves 14 and 16 or 15 and 17 provided on the head of the said implant. These two legs 10 and 12 are shown, before the bending operation, in the FIG. 19A and after the bending operation, in the FIG. 2. Thus bending the two legs 10 and 12 into the grooves 14 and 16 or 15 and 17 after screwing the head 9 on the body of the said implant it is possible to block the head perfectly and thus all risk of unscrewing of the said head during the chewing operation is avoided. The head 9 of the implant, as it is shown in the FIGS. 4 to 6 is provided with a cylindrical end comprising the grooves 14, 15, 16 and 17. The said cylindrical end is followed by a central spherical portion which in its turn is followed by another cylindrical end of the same diameter as the portion 7 of the body of the implant. This particular end of the head 9 is provided with a cavity having a complementary profile of the portion 7" of the body of the implant and its surface is provided with four grooves 18, 19, 20 and 21 as shown in the FIGS. 5 and 6. The head 9 is also provided with a central threaded hole so that it can be screwed on the portion 9 of the body of the implant. The existence of these grooves 18, 19, 20 and 21 offer the possibility to increase the elasticity of the walls which may be slightly expanded in course of the screwing operation of the head 9 on the portion 8 of the body of the implant because the male conical portion 7″ forces progressively into the female conical cavity of the head 9, and so one can increase considerably the adherence of the implant inside the bone during the post operation bone growing process. However once the bone is reformed into the grooves 18, 19, 20 and 21, any possibility of rotation of the implant is avoided. I mention here that the conicity of the portions 3 and 5 of the implant are designed in accordance with the standard Morse cone forms as utilized to fix the conical drill shanks on the driving head of a drilling machine. This solution offers a solid adherence between the body of the implant and the corresponding profiled cavity, machined into the maxillary and thus increases considerably the bearing surface on the bone in comparison with the actually utilized implants by producing an effect similar to a conical clutch. Thus this particular solution offers the possibility to obtain a better stress distribution on the bone surface and consequently an appriciable reduction of the intensity of pressure on the bearing surface can be achieved.

Figure 7:
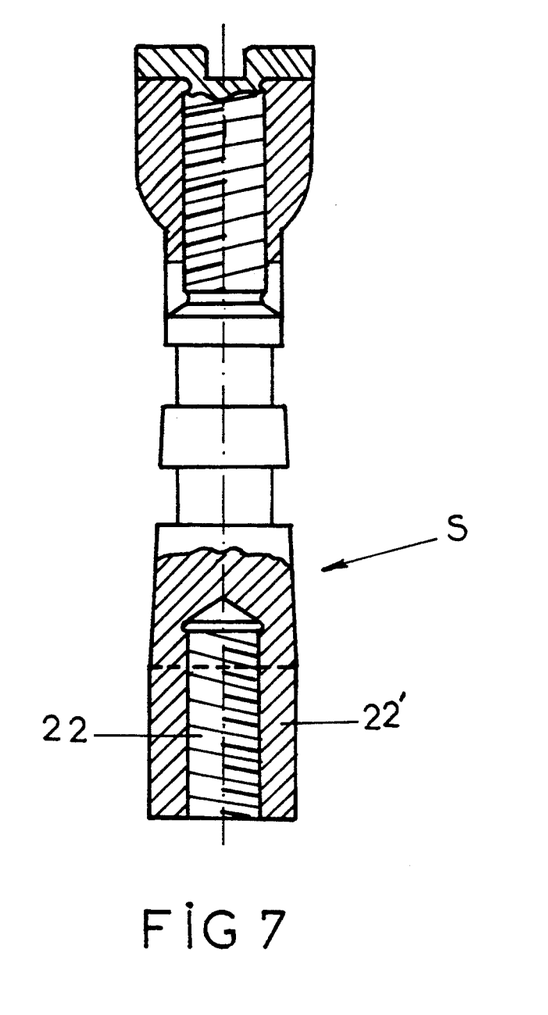
Figure 8:
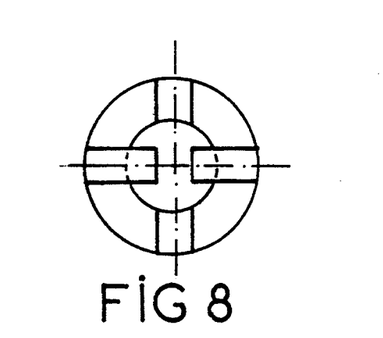
Figure 9:
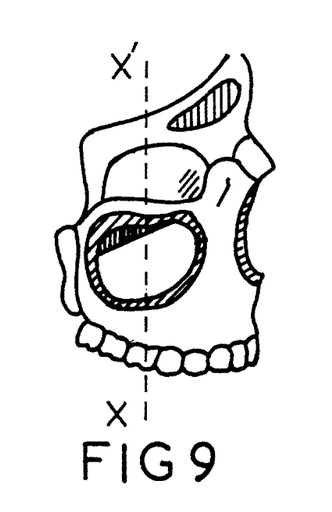

A second mode of realization derived from the said implant S of FIG. 2 is shown in the FIG. 7 bearing the reference S′. One can observe on the FIG. 7 that the threaded portion 1 of the first mode of realization of the implant is replaced and the cylindrical portion 22′ is longer than the portion 2 of the FIG. 2, which permits to provide a threaded hole 22 sufficiently long which can be utilized later to fix any suitable dental prosthetic appliance. It is understandable that the remaining portion of the implant is kept perfectly identical as the first mode of realization. It is particularly interesting to observe that the system of implant according to this invention do not require the necessity to tap threads in the spongy bone during its installation as the assembly of the threaded portion is produced only on metal to metal surfaces. However the implantation of the above described implants needs the utilization of an assembly of specially adapted instruments. These instruments are indispensable and consequently they form an integral part of the present invention and should be considered as a means to realize the goal of the invention as per example the implantation of the said dental implant in the mouth of a patient. The following part of the description is intended to give a detailed description of the said special instruments, which in my knowledge are new and not commercialized as yet in the dental technology.

Figure 17:
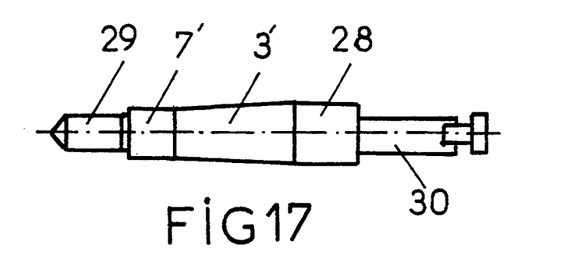

The FIG. 17 shows a first profiled milling tool having different profiled portions. The cylindrical portion 28 of the said tool is provided with a diameter which is the same as the portion 2 of the implant. The portion 3′ of the said tool is profiled in such a manner to obtain a continuous conical surface, having the same conicity as the portion 3 and 5 of the implant as shown in the FIG. 2. The length and the dimension of that portion 3′ of the milling tool correspond exactly with the conical portion of the implant of the FIG. 2 with the difference that the grooves 4 and 6 are eliminated here to obtain the said continuous conical surface. The cylindrical portion 7′ has the same diameter as that of the portion 7 of the implant shown in the FIG. 2 but it may have different lengths. Consequently an assembly of milling tools of different lengths for the said portion 7′ is foreseen in order to be able to obtain a proper correspondence of the portion 7′ with the portion 7 of the implant according to each particular case. As the available thickness of the bone is different for every case, a set of dental implants having different lengths should be provided. This particular factor is very important for the industrialization in mass scale manufacturing process because it is possible to obtain a complete set of implants with corresponding milling tools only by changing the length of the portion 7 and 7′ and thus keeping all other portions identical, not only for the milling tool but also for the implant. The said milling tool is also provided with a cylindrical portion 29 which is intended firstly to guide the movement of the profiled portion in the primary hole drilled previously into the bone using an ordinary twist drill, and secondly, when the said portion 29 bigins to come out through the floor of the sinus, one can have the exact idea of the length of penetration of the said profiled portion of the milling tool into the bone by measuring the length of the said portion 29 projecting outwards from the bone surface. The portion 28 of the milling tool is provided with a leg 30 having a normal shape as utilized currently for dental milling tools in a normal dental unit.

Figure 18:
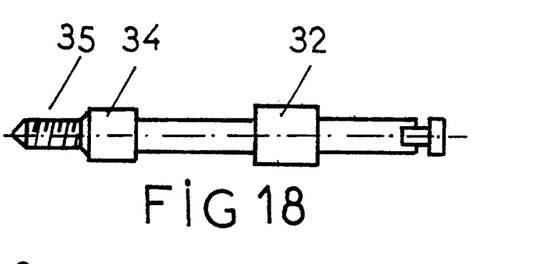
Figure 19:
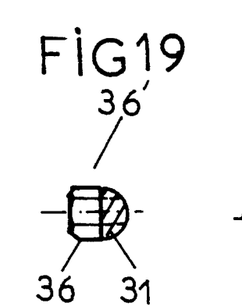
Figure 19A:
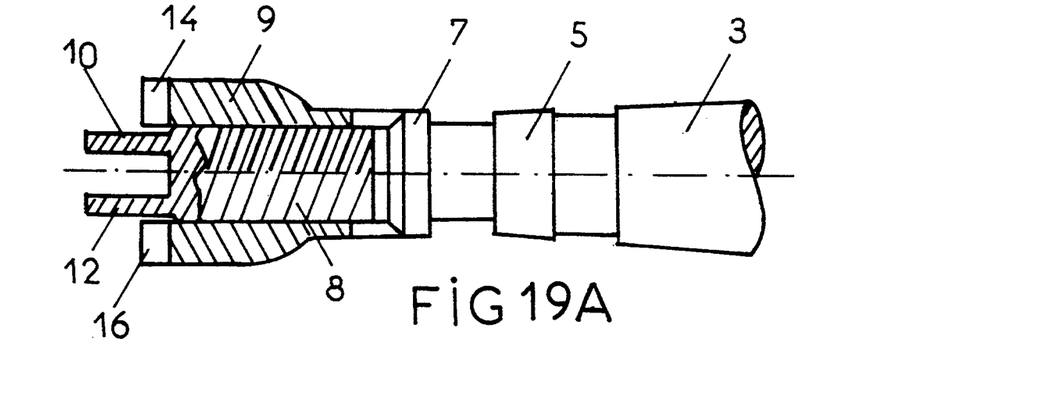

The FIG. 18 shows a mandrel provided also with different portions for driving a second milling tool 36′ having a particular shape as represented in the FIG. 19. The said mandrel is also provided with a driving leg simillar to the milling tool represented in the FIG. 17. The said leg is followed by a cylindrical portion 32 having the same diameter as that of the portion 28 of the milling tool shown in the FIG. 17. The said mandrel is provided with a second cylindrical portion 34 having the same diameter as the portion 7′ of the milling tool shown in the FIG. 17. The said two cylindrical portions 32 and 34 are connected by a rod 33 to form a single unit. The opposite end of the driving leg is provided with a threaded cylindrical portion 35 which is intended to receive a second milling tool 36′ having two different portions 31 and 36 as it is represented in the FIG. 19. The said second milling tool 36′ is designed as a normal nut having a hexagonal head 36 fixed on another portion 31 of spherical shape bearing a cutting element. The whole assembly is traversed by a threaded hole in order to be screwed on the portion 35 of the mandrel represented in the FIG. 18 and consequently to be driven by the same. I like to mention here that the portion 32 and 34 are utilizable as a guiding means during the milling operation of the spherical cavity concentrically to the hole drilled by the first milling tool of the FIG. 17.

Figure 20:
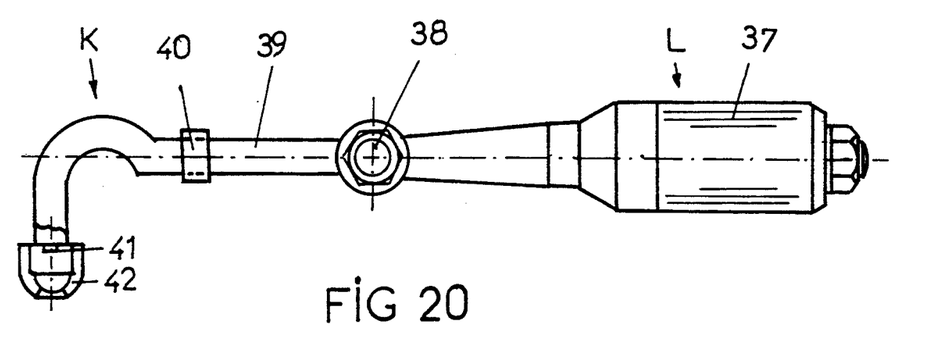
Figure 21:
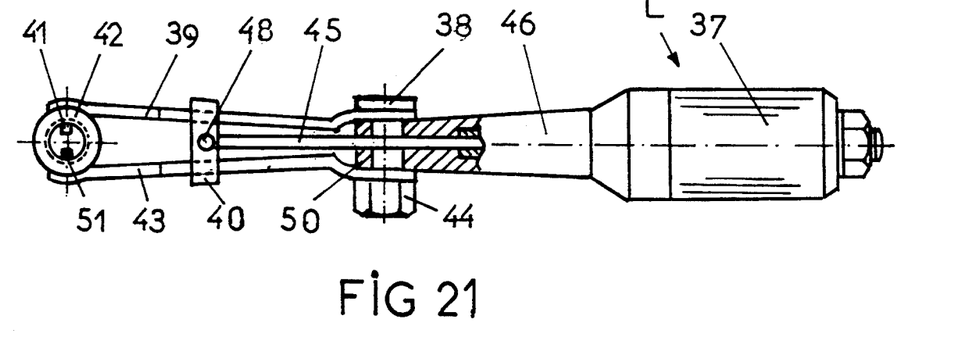

The FIGS. 20 and 21 show a holding tool having a remote control system which offers the necessary manipulating facility during the operation procedure for the head of the implant 9 and the milling tool 36′ during their installation or removal into or from the selected position inside the sinus or nasal cavity according to the case. The said tool comprises two principal elements generally represented by references L and K. To simplify the description the element L will be called "The handle" which could be grasped by the surgeon during operation. The element K will be called "The grasping head". As it is shown in the FIGS. 20 and 21 the two elements L and K are assembled by a bolt 38 and a nut 44 in such a manner that the axis of the grasping head K can be rotated about the axis of the bolt 38, while the nut 44 is not tightly screwed. Thus it is possible to find out an angular orientation of the grasping head K in relation to the handle L according to the desire of the operator. The grasping head K comprises two hands 39 and 43 made of thin spring steel sheets, which are punched, bent to form and tempered to obtain the profile as designed in the FIGS. 20 and 21. One of the ends of each hand is provided with a cap of hemispherical form, as represented by the reference 42, on the hand 39, in the FIGS. 20 and 21. When the hands 39 and 43 are placed in the working position, the two hemispherical caps are assembled together to form a cavity of a particular shape which can maintain the head 9 of the implants S and S' or the milling tool 36 as it may be required during operation. Two figures 41 and 51 are provided on each said cap in order to prevent the rotation of the head 9 of the implant during the screwing operation to assemble the head 9 on the threaded portion 8. The other end of each hand 39 and 43 is slightly bent and drilled to obtain the shape as shown in the FIG. 21, so that they can be mounted on one of the ends of the handle L by the bolt 38 which works also as the axis of rotation. The two hands 39 and 43 are provided with a straight portion to receive a mobile cursor 40. The displacement of the said cursor 40 towards the left brings the hands 39 and 43 near to each other for the closing operation and on the contrary, for opening the same, one should displace the cursor 40 towards the right, so that the hands 39 and 43 move away from each other. The said cursor 40 is actuated with the help of a piano cord 45 fastened to the pin 48 passing through the cursor 40. The other end of the said piano cord 45 is passed at first through a hole provided in the said bolt 38 and then welded on a rod 49 placed inside the handle L as shown in the FIG. 22. The proper function of the said rod 49 and the cord 45 will be exposed later.

Figure 22:
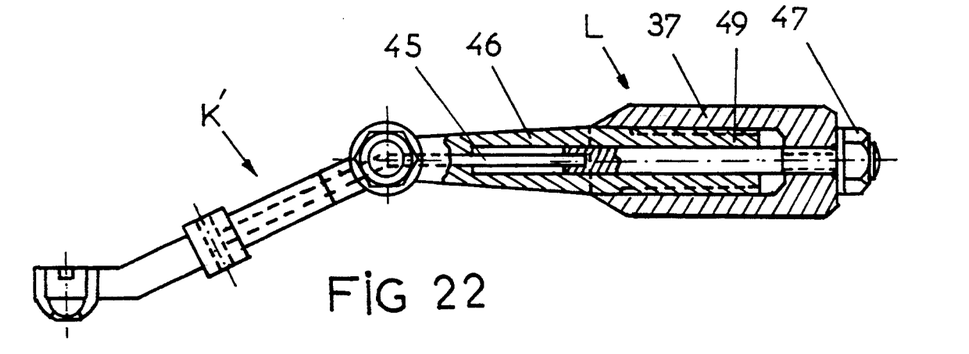

The handle L as it is shown in the FIGS. 20, 21, and 22 is composed of three different elements. The first element 46 bears at it's left end a cylindrical head comprising two surfaces which are parallel to the axial line of the handle. The said head is provided with a hole to make a passage for the bolt 38. The said head is also followed by a conical portion and ending with a cylindrical threaded portion. The element 46 is provided with an axial longitudinal bore extending through the major portion of its length. The second element 46 is shaped as a socket which is knurled externally and threaded internally. A third element, composed with a rod 49, may slide in the central bore of the element 46. As it is mentioned above, one of the ends of the rod 49 is fixed to the piano cord 45 by welding, while the other end is provided with a threaded portion. As it is shown in the FIG. 22, the said threaded portion of the rod 49 is designed to get through the socket 37 by using a hole provided in the said socket. An adjusting nut 47 is screwed on the threaded portion of the said rod 49. This conception gives the possibility to adjust the overall length of the assembly composed by the rod 49 and the piano cord 45 between the axis of the cursor 48 and the right end face of the socket 37, while it is intended to change the working angle between the center line of the handle L and the center line of the grasping head K. A blocking nut, not shown, may be utilized to retain the nut 47 to prevent unscrewing. On the FIGS. 20 and 21, the grasping apparatus is shown with it's hands in closed position, and the cursor 40 is represented in it's extreme left position. If now one turns the socket 37 in anticlockwise direction, the said socket 37 during it's displacement in the right hand direction, draws the cursor 40 with the help of the rod 49 and the piano cord 45, as both of them moves together simultaneously with the socket 37. As long as the said cursor moves to the right, the two hands 39 and 43 continue to open by utilizing the spring effect and thus disengage the element retained into the caps 42.

The FIG. 22 shows another grasping head K' which can be mounted in the same handle L. The two said grasping heads K and K' have identical working principle; only the shape of their hands are different. Anyway it is easy to design other forms of interchangeable hands which can be mounted on the same handle L using the same working principle as mentioned above.

For a better understanding of the invention, concerning application, the following portion of the description will be reserved to expose a detailed installation procedure for the implant described above, into the mouth of a patient. This procedure is composed of different steps.

Figure 15:
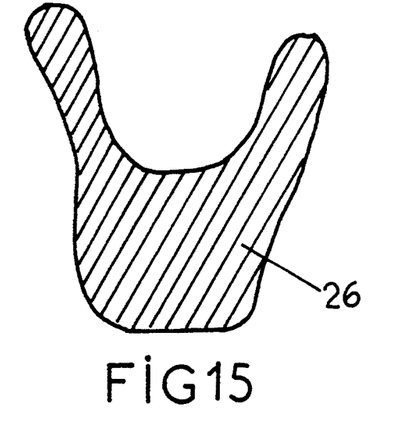
Figure 16:
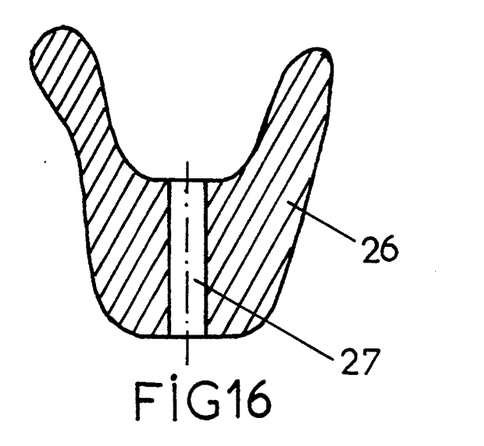

Before the beginning of the specified surgical operation, the first step of the said procedure for installation of the said implant is to make a mould of the upper maxillary with "Alginate" and then to prepare a "Cradle-splint" in resin sufficiently thick, in a dental laboratory, as indicated by the reference 26 in the cross sectional view shown in the FIG. 15. A hole 27, perpendicular to the maxillary plane is now drilled into the said "Cradle-splint" exactly in the desired position of implantation of the said implant as shown in the FIG. 16. The said "Cradle-splint" after drilling is now placed on the maxillary as shown in the FIG. 11 and a first hole 24 is drilled in the maxillary, by utilizing the said hole 27 to guide the drilling tool. The diameter of the holes 27 and 24 are the same as the diameter of the portion 29 prescribed on the milling tool of the FIG. 17.

The second step is similar to the classical operation of CALDWELL-LUC for the trephining of the maxillary sinus through the access of the eye tooth cavity according to the following sequence of operation procedure:

Making a horizontal incision, at least two to three centimeter long, directly up to the bone on the gum, at a distance about one centimeter from the free end of the gum.

Figure 1:
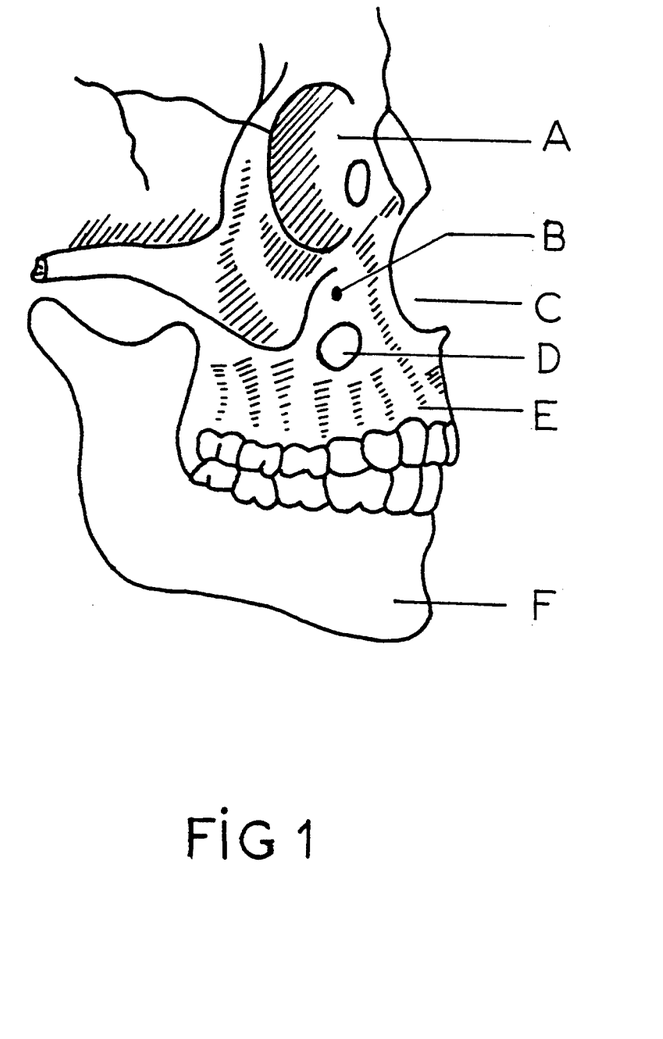

Scraping of the back portion of the eye tooth cavity upwardly saving carefully the sub-orbitary nerve cavity B shown in the FIG. 1.

Figure 10:
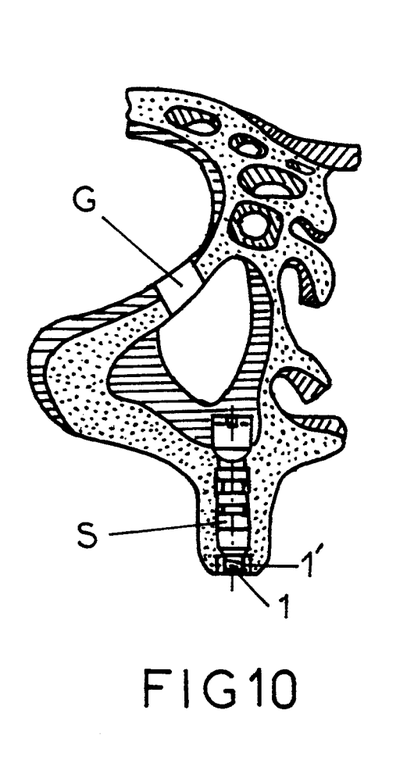

Perforation of the eye tooth cavity with the help of a classical bone milling tool under the emergence of the sub-orbitary nerve B. The said perforation, represented by the reference D in the FIG. 1 and more in detail in the FIG. 10 by the reference G, has a dimension sufficient to be able to pass the pulp of the index finger. Preferentially the center of the said perforation D is placed in front of the axis of the bore 24 as represented in the FIG. 11. Naturally, the surgical steps of this operation should be followed minutely with maximum sterilization, using rotary tools at reduced speed and advancing slowly with small touches in order to avoid any heating of the bone.

Figure 10A:
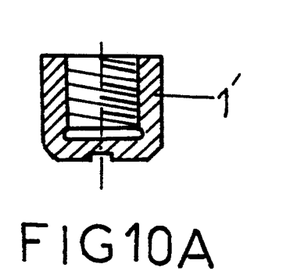
Figure 11:
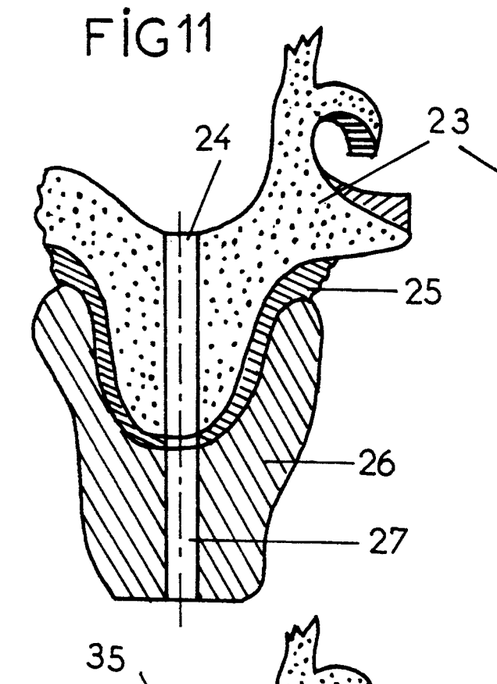
Figure 12:
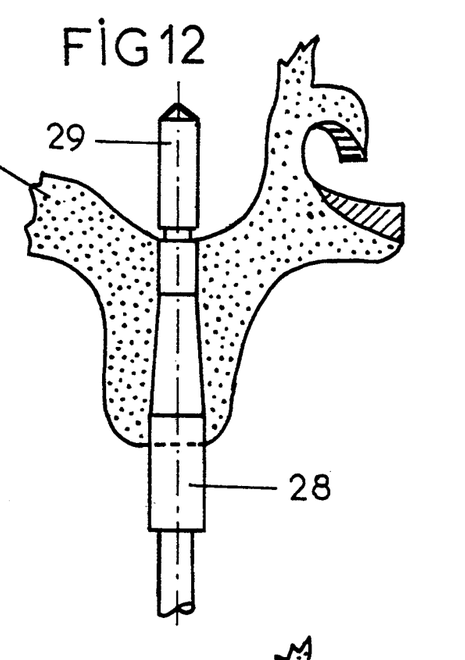
Figure 13:
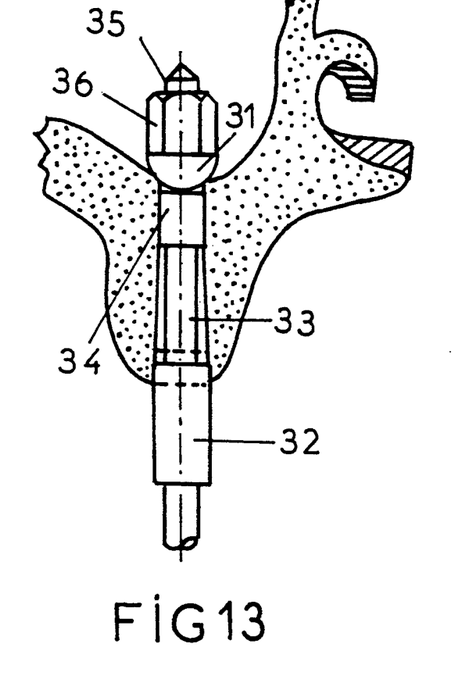
Figure 14:
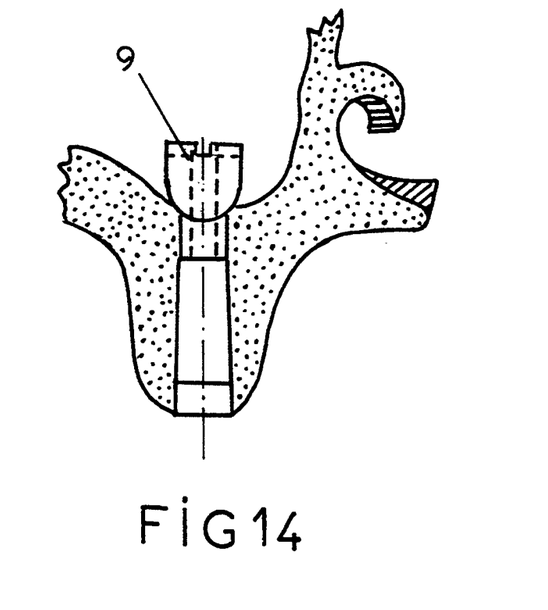

In the third step of the operation, the bore 24 of the FIG. 11 is transformed in a hole, having strictly the profiled shape of the implant. The said transformation is achieved by utilizing the profiled milling tool as designed in the FIG. 17, by introducing the portion 29 into the hole 24, and thus remaining constantly guided during the milling operation to obtain a perfect alignment. Then the said tool is progressively advanced in the upward direction until the whole length of the portion 29 becomes visible through the hole D as shown in the FIG. 12. Thus one can obtain a cavity whose shape is perfectly identical with that of the implant and having it's axis perfectly perpendicular to the maxillary. Afterwards the first profiled milling tool is withdrawn and then the mandrel represented in the FIG. 18 is introduced into the said cavity. Now by using the grasping apparatus of FIGS. 20 and 21, one can screw in the second milling tool, represented in the FIG. 19, on the portion 35 of the said mandrel by passing the said tool through the hole D shown in the FIG. 1. The FIG. 13 shows the said mandrel assembled with the second milling tool and the way it should be placed in the reserved cavity for the implant. It should be noticed here, that the portion 34 and 32 of the said mandrel allows it to be maintained in perfect alignment with the said cavity reserved to receive the implant. Then the said mandrel assembled with the said milling tool is driven with the help of a classical rotary equipment and by drawing the said assembly slowly in the downward direction one can produce a spherical seat having exactly the same shape as the spherical portion of the head of the implant. Afterwards one can screw out the said second milling tool and then it is taken out through the hole drilled in the sinus by using the same grasping instrument, and finally the mandrel is withdrawn through the mouth hole. Now one can definitely place the head 9 of the implant in it's reserved loging position, as shown in the FIG. 14 with the help of the said grasping instrument always by passing through the sinus hole D. By retaining the head 9 of the implant with the said grasping instrument one can now introduce the implant S or S' from below into the cavity reserved for it's reception and then by turning the body of the implant, one can screw in the portion 8 into the head 9 in the way as represented in the FIG. 19A. When the head and the body of the implant are perfectly assembled, the external surface of the implant coincide perfectly with the internal surface of the cavity and the floor of the sinus. Now by utilizing the sinus hole it is possible to bend the legs 10 and 12 into the slots 14 and 16 as it is represented in the FIGS. 2, 3, 4 and 5. Once the implant is placed definitely and perfectly secured in position as it is shown in the FIG. 10, a careful suture of the mucous muscular surfaces of the eye tooth cavity is performed to form one plain. As the bottom portion of the final implant coincide with the bone surface it is necessary to suture the the gum to sink the said implant inside during the period of osteogenesis. This osteogenesis will contribute to increase the strength of the implant. It is necessary to recall here that the total length of the implant should be adapted to each particular case and in order to achieve that the projecting portion outside the bone under the gum should be cut out, once the said implant is definitely installed in place. In case of the S type implant as shown in the FIG. 10 after final installation, the length of the threaded portion 1 is adjusted in such a manner that one can screw the cap 1' to protect the threads from the bone deposits during the bone growing period and to fill up the void space around the said threaded portion. The said cap is shown in a bigger scale in the FIG. 10A. A slot to receive a screw driver is provided on the bottom portion of the said cap for the screwing or unscrewing of the same. During the preparation of the sub-osseous prothesis, the said cap 1' is taken out in order to utilize the threaded portion 1 as an anchoring means for the prothesis.

By reducing the height of the head of the said implant, represented by the reference 9 in the FIG. 2, one can utilize the same on the level of the central or the lateral incisive zone. In that case, the head 9 is introduced into the mucous covering the floor of the nasal cavity after preparation of the nasal bone floor.

The said implants S or S' is particularly but not exclusively designed to compensate the gap left by a lost tooth on the upper maxillary. It is quite understandable, that before taking any decision for the operation it is necessary to establish a complete medical survey of the patient in order to avoid classical inacceptable cases suffering from the disease as follows:

Cardiac affection
Diabetes
Bone diseases
Blood complications
Cancer
Allergic to general or local anaesthesia
Sida
Degenerative diseases
Psychic illness Once the general medical survey is achieved, a complete local survey is done usually by using adequate X-ray systems, in order to know exactly the volume of the maxillary sinus and also the existant bone volume between the maxillary sinus floor and the edge of the alveolus. The said surveys are very important for the choice of the exact dimensions of the implant suitable to satisfy every case. This type of implatation can only be realized on healthy bones and on the sinus free from any affection, by utilizing polyvalent antibiotherapic protection and under maximum antiseptic precaution. Once the operation is achieved, a complete X-ray control is carried out to make a final verification and to assure a good positioning of the implant in the mouth of the patient.

The invention claimed is:

1. A dental implant for installation in the maxillary comprised of a body and a head, said body is provided with a threaded end for attaching a dental prosthesis, said threaded end is connected to a first cylindrical portion which is connected to a first truncated conical portion, which in turn is connected to a second cylindrical portion having a diameter smaller than the smallest diameter of said truncated conical portion, said second cylindrical portion is further connected to a second truncated conical portion having the same conicity as said first truncated conical portion and said first and second truncated conical portions being coaxially disposed such that their conical surfaces will mate with the internal surface of a prepared maxillary cavity, said second truncated conical portion is further connected to a third cylindrical portion which has a diameter smaller than the smallest diameter of second truncated conical portion, said third cylindrical portion is further connected to a fourth cylindrical portion coaxial with said first and second truncated conical portions, said fourth cylindrical portion having a base at the side connected to said third cylindrical portion and having a diameter equal to the diameter of the conical projection, onto said base of the fourth cylindrical portion, of a cone defined by the first and second truncated conical portions, said fourth cylindrical portion is further connected to a third conical portion having an inclination of thirty degrees which in turn is connected to a fifth cylindrical portion, said fifth cylindrical portion is provided with threads for receiving said head, said fifth cylindrical portion having a split portion forming two legs which can be bent into slots formed on said head, whereby said head is prevented from rotation to lock the head against unthreading.

2. The dental implant of claim 1 wherein said head has a cylindrical end having a plurality of bearing slots for receiving said legs, said head cylindrical end is connected to a central spherical portion which in turn is connected to a second cylindrical end, said cylindrical end having a diameter equal to the diameter of said fourth cylindrical body portion and having a conical shaped cavity complementary to said third conical body portion for mating therewith, said cylindrical end of said head further having four slots for increasing the elasticity of the mating end, said second cylindrical end of said head further having a central threaded bore for threading said head onto said fifth cylindrical portion of said body, whereby, by progressively forcing the third conical portion of said body against the conical cavity of said head, the elasticity of said head end portion increases the locking of the head and body.

3. The dental implant of claim 1, wherein the conicity of the first and second truncated conical portions of said body correspond with a standard conicity for drills used to form the cavity in the maxillary, whereby, a tight friction fit is obtained when implanted.

4. The dental implant of any one of claims 1, 2 or 3 wherein said threaded end of said body for attaching a dental prosthesis comprises an external threaded surface upon which a dental prosthesis can be threaded.

5. The dental implant of any one of claims 1, 2 or 3 wherein said threaded end of said body for attaching a dental prosthesis comprises an elongated internal threaded cylindrical portion into which a dental prosthesis can be threaded.

* * * * *